(12) United States Patent
Bay et al.

(10) Patent No.: US 8,826,173 B2
(45) Date of Patent: Sep. 2, 2014

(54) GRAPHICAL INTERFACE FOR THE MANAGEMENT OF SEQUENTIAL MEDICAL DATA

(75) Inventors: Susanne Bay, Erlangen (DE); Lutz Gündel, Erlangen (DE); Labib Khanafer, Nürnberg (DE); Ralf Krumtünger, Nuremberg (DE); Matthias Thorn, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1438 days.

(21) Appl. No.: 12/152,231

(22) Filed: May 13, 2008

(65) Prior Publication Data
US 2009/0083664 A1 Mar. 26, 2009

Related U.S. Application Data

(60) Provisional application No. 60/975,229, filed on Sep. 26, 2007.

(51) Int. Cl.
*G06F 3/00* (2006.01)
*G06F 19/00* (2011.01)
*G06F 3/048* (2013.01)

(52) U.S. Cl.
CPC .............. *G06F 19/322* (2013.01); *G06F 3/048* (2013.01); *G06F 19/3406* (2013.01)
USPC ............ 715/792; 715/804; 715/200; 715/232

(58) Field of Classification Search
CPC ....................................................... G06F 3/048
USPC .................................. 715/792, 804, 200, 232
See application file for complete search history.

(56) References Cited

U.S. PATENT DOCUMENTS

| | | | |
|---|---|---|---|
| 5,914,715 A * | 6/1999 | Sasaki ........................... | 715/803 |
| 7,010,751 B2 * | 3/2006 | Shneiderman ................ | 715/232 |
| 7,058,901 B1 * | 6/2006 | Hafey et al. ................... | 715/792 |
| 7,099,798 B2 * | 8/2006 | Yu et al. ........................ | 702/186 |
| 7,415,662 B2 * | 8/2008 | Rothmuller et al. .......... | 715/200 |
| 7,895,527 B2 * | 2/2011 | Zaleski et al. ................ | 715/804 |
| 2005/0055625 A1 * | 3/2005 | Kloss .......................... | 715/500.1 |
| 2006/0031017 A1 | 2/2006 | Mathieu et al. | |
| 2006/0265249 A1 * | 11/2006 | Follis et al. ....................... | 705/3 |

FOREIGN PATENT DOCUMENTS

WO WO 2004/034910 A1 4/2004

* cited by examiner

*Primary Examiner* — Michael Roswell

(57) ABSTRACT

The invention relates to a method for generating on at least one display device a graphics display of data descriptors. The data descriptors, describing items of data, are arranged on an interactive timeline as interactive timeline elements along with interactive data elements. The interactive timeline elements and the interactive data elements allow retrieval of the items of data.

17 Claims, 5 Drawing Sheets

GRAPHICAL INTERFACE FOR THE MANAGEMENT OF SEQUENTIAL MEDICAL DATA

CROSS REFERENCE TO RELATED APPLICATIONS

The present application claims the benefit of the provisional patent application filed on Sep. 26, 2007, and assigned application No. 60/975,229, which is incorporated by reference herein in its entirety.

FIELD OF THE INVENTION

The present invention relates to medical and clinical engineering, and more specifically to method and a system for the management of sequential medical data.

BACKGROUND OF THE INVENTION

One of the tasks of medical practitioners is to make a diagnosis based on medical data. The medical data holds information pertaining to a condition of a patient. The medical data is available as medical images or in written form, such as laboratory reports. The medical images and the other medical data, collectively called studies, are acquired from medical imaging techniques such as computer tomography (CT), PET or X-ray. The medical practitioner uses a large number of studies which he or she inspects visually in order to establish a diagnosis or to monitor the patient's condition during a course of treatment. One of the approaches taken is to inspect successively a sequence of studies in a chronological order. This approach allows the medical practitioner to ascertain trends and developments in the patient's condition. For example, CT slices of a body part inflicted with a tumour are acquired over a period of time and are visually compared using post-processing software, e.g. "viewers". The medical practitioner visually compares a series of CT slices obtained by searching and selecting one CT slice per week from all of the acquired CT slices acquired. The slice, a "prior", is representative for that week. A number of representative CT slices from various weeks are for example compared with each other or with another CT slice taken before treatment commenced, termed the "baseline" image. In this way, the growth or degradation of the tumour can be monitored over time.

Currently, the medical practitioner, upon querying a number of databases, draws up a list of images that he wishes to inspect, retrieves the images and loads the images manually into a viewer. This approach is rather cumbersome and prone to many errors when inspecting the studies.

The medical practitioner must often for the purposes of differential diagnosis consider and "cross-inspect" images of different kinds and in different formats. This includes studies acquired using different equipment. A variety of different viewers is normally needed.

When drawing up the list of images, the medical practitioner must make a choice as to a time resolution at which he wishes to view the series of images. In the example of the tumour discussed above in which one image for each week is selected, a time resolution has been chosen to be a weekly one. However, in the course of a differential diagnosis, for example, it may be necessary to view the series of images at a finer time resolution, for example specified by daily intervals rather then weekly intervals. Therefore, the medical practitioner will have to repeat the procedure outlined above. In this repeat study the medical practitioner will select one study for each consecutive day from the list of images.

Once the medical practitioner has finally compiled the list of the images of interest after searching, selecting and sorting them, he or she will have to load each ones of the images into the viewer. The medical practitioner will need to be aware of a rank (baseline, current, prior 1, prior2, etc) of the study currently being viewed. His or her attention is thus distracted as he or she will frequently have to keep an eye on the list of images of interest in order to determine the rank. This method can become unwieldy if he or she has to toggle between several ones of the studies of interest.

It will be useful to provide a user interface, which allows the medical practitioner to carry out in an intuitive and interactive manner visual examination of a large number of sequential data. More specifically, there is a need for a user interface permitting multiple ways of viewing a large number of items of sequential data of different formats for the purposes of comparison of the items of sequential data. Furthermore there is a need to be able to efficiently adapt a time resolution at which the medical practitioner wishes to conduct a visual inspection of the studies A current system for managing medical data is, for example, disclosed in the applicant's US patent application 2006/0031017. This application relates to interpolation and merely teaches how to generate intermediate images for a sequence of images. Teachings as to alleviate the burden on the user in interfacing with sequential data are not disclosed.

US patent application WO 2004/034910 discloses a display processor for representing data in a composite display.

It will be appreciated that the invention may be put into good use wherever there is a need to manage and examine large amounts of items of data in different formats. The data represents a snapshot of the state of a system at a time. By using the invention for examining such items of data, the behaviour of a complex system can be analyzed to detect trends. One example in addition to the medical examples discussed above is for the purposes of fault diagnosis.

SUMMARY OF THE INVENTION

One aspect of the present invention addresses these needs by providing a method for generating on at least one display device a graphics display of a plurality of data descriptors arranged on an interactive timeline. The interactive timeline comprises a plurality of interactive timeline elements, the interactive timeline elements being associated with time points and ones of the plurality of data descriptors are associated with ones of interactive data elements.

The method comprises displaying at least one of the time points as one of the interactive timeline elements. At least one of the plurality of data descriptors associated with the displayed at least one of the time points is selected. The selected at least one of the plurality of data descriptors are displayed in a template as one of the ones of the interactive data elements. Further ones of the plurality of data descriptors associated with the displayed at least one time of time data are selected and the further selected ones of the plurality of data descriptors are displayed.

According to one aspect of the present invention, the items of data descriptors describe items of data having time stamps.

According to another aspect of the present invention, the interactive data elements allow retrieving one of the items of data by a navigation device. The one of the items of data are being described by the displayed one of the selected at least one of the plurality of data descriptors.

According to one another aspect of the present invention, selecting at least one of the plurality of data descriptors associated with the displayed at least one of the time points comprises grouping the items of data based on the time stamps and aggregating the ones of the plurality of data descriptors describing same ones of the grouped items of data.

According to one another aspect of the present invention, the grouping is further based on further ones of the plurality of data descriptors and pre-definable rules. The pre-defined rules prescribe grouping relations between the ones of the plurality of data descriptors. For example, a predefined rule might be to group CT images and PET images together, even though they have not been acquired on the same day.

According to one aspect of the present invention, the at least one time point being displayed as one of the interactive timeline elements is representative of the time stamps of at least one of the same ones of the grouped items of data. According to another aspect of the present invention, upon retrieval of one of the grouped items of data by means of one of the interactive data elements, the at least one time point displayed on that interactive date element is capable of being set apart visually from the interactive timeline. This aspect lets the user immediately understand what time point the retrieved item of data belongs to.

According to another aspect of the present invention, a further time point is displayed as a further interactive timeline element. The more than one time points are arranged as more than one of the interactive timeline elements on the interactive timeline in a chronological order. This aspect facilitates temporal navigation trough and retrieval of items of data.

According to another aspect of the present invention, the more than one of the interactive timeline elements displaying the more than one of time points allow more than one of the at least one of the same ones of the grouped items of data to be retrievable for the purposes of mutual comparison.

According to another aspect of the present invention, the displayed at least one time point is visually associated with the displayed ones of the aggregated ones of the plurality of data descriptors. The user perceives at one glance what kind of data is available for each time point.

According to another aspect of the present invention, the displaying of the at least one time point as one of the interactive timeline elements is suppressed if there are no grouped ones of the items of data whose time stamps can be represented by the displayed time point. This aspect allows focusing the user's attention to relevant time points only.

According to another aspect of the present invention, a further template is being displayed on the graphics display device. The further template displays further ones of the aggregated ones of the ones of the plurality of data descriptors in response to detecting an event. This aspect allows the user to learn more about the items of data. The user can better make a decision whether to retrieve the item of data or not. Unnecessary retrievals based on mere guessing are kept low and loads on an underlying retrieval device and communication means can be kept to a minimum.

According to another aspect of the present invention, a further one of the at least one time point is displayed as a further one of the one of the interactive time line elements, if the further one of the one of the interactive time line elements is displayable in the definable template. If the at least one of the further one of the interactive time line elements is not displayable in the pre-definable template, a format of the defined template is adjusted. This aspect helps keep the graphics display from being overloaded with information.

According to another aspect of the present invention, the adjusting the format of the defined template includes but is not limited to hiding some of the interactive time line elements.

According to another aspect of the present invention, the adjusting the format of the defined template includes but is not limited to adding a scrolling element to the defined template.

According to another aspect of the present invention, an interactive time line event is received, the event being indicative of the navigation device interacting with the one of the interactive timeline elements, displaying the at least one time point. In response to the interactive timeline event, at least one of the items of data is being retrieved. The at least one time point is representative of the time stamp of the retrieved one of the at least one item of data.

According to another aspect of the present invention, an adjustable time unit for adjusting a time resolution on the interactive timeline is being received. This aspect lets the user choose a comfortable time unit for navigating through the items of data. A proper time resolution facilitating detection of information such as trends and developments being derivable from the items of data is made possible.

According to another aspect of the present invention, the at least one time point, being representative of the time stamps of the grouped items of data, equals substantially a multiple of the received time unit. By this aspect the user can have the time points designate time units, for example "first week", "second week" etc referring to a user's local system time for example.

According to another aspect of the present invention, the at least one time point, being representative of the time stamps of the grouped items of data, equals any one of a time indicative of any one of the time stamps of the grouped items of data.

According to another aspect of the present invention, items of data relate to medical purposes.

According to another aspect of the present invention, the data descriptors comprise metadata.

According to another aspect of the present invention, upon receiving a signal from the user, the at least one of the plurality of descriptors associated with the at least one of the displayed time points are merged with at least a further one of the plurality data descriptors associated with a further one of the displayed time points. The merged data descriptors are associated with either the at least one of the displayed time points or the further one of the displayed time points.

Yet another aspect of the present invention addresses these needs by providing a computer-readable medium having computer-executable instructions for performing the method according to the method above.

Another aspect of the present invention addresses the needs above by providing a system for displaying on a display device a graphics display of a plurality of data descriptors. The data descriptors describe items of data having time stamps. The plurality of data descriptors are arranged on an interactive timeline. The interactive timeline comprises a plurality of interactive timeline elements.

Ones of the plurality of data descriptors are associated with interactive data elements. The interactive data elements allow the items of data being described by the ones of the plurality of data descriptors to be retrievable by at least one navigation device.

The system according to the present invention comprises a data interface module operative to grouping, based on the time stamps, the items of data.

There is also a data aggregator module operative to aggregating the ones of the plurality of data descriptors describing same ones of the grouped items of data.

Further there is a time graphics display manager operative to displaying on the interactive timeline at least one time point as one of the interactive timeline elements, the at least one time point being representative of the time stamps of at least one of the same ones of the grouped items of data.

Yet, further, there is a data graphics display manager operative to displaying the aggregated ones of the ones of the plurality of data descriptors in a definable template as ones of the interactive data elements.

According to one aspect of the present invention, the graphics display manager is operative to associating the displayed at least one time point with the displayed ones of the aggregated ones of the ones of the plurality of data descriptors.

According to another aspect of the present invention, the system further comprises a user data interface operative to receiving an adjustable time unit for adjusting a time resolution on the interactive timeline.

According to another aspect of the present invention, the system further comprises an application manager operative to receiving an interactive time line event indicative of the navigation device interacting with the one of the interactive timeline elements displaying the at least one time point. In response to the interactive timeline event, at least one of the items of data is being retrieved, the at least one time point being representative of the time stamp of the retrieved one of the at least one item of data According to another aspect of the present invention, the navigation device is selected from the group consisting of cursor, pointer or touch screen.

According to another aspect of the present invention, the plurality of data descriptors is selected from the group consisting of a patient identification, body part, type of examination, name of study, medical image, further medical data and a diagnosis.

BRIEF DESCRIPTION OF THE DRAWINGS

The invention is described in more detail with reference to the drawings, in which.

DETAILED DESCRIPTION OF THE INVENTION

In the following detailed description of the embodiments, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the present inventions. The following detailed description is, therefore, not to be taken in a limiting sense, and the scope of the present inventions is defined only by the appended claims.

As will also be apparent to those skilled in the art, the graphics display 100 encompasses alternate embodiments of a software program in which the functions of the system are performed by modules different to those shown in the Figures. The graphics display 100 may process items of data in a serial or parallel fashion, or in a combination of the two, without departing from the spirit or scope of the invention. The software program may be written in one of several widely available programming languages and the modules may be coded as subroutines, subsystems, or objects depending on the language chosen. Similarly, the items of data used by the graphics display 100 are described and represented as files resident in a directory hierarchy of a data storage facility but the invention is not limited to the described arrangement of the items of data, nor is the use of any particular type of data management system implied.

The term "items of data" refer to any kind of electronically stored and retrievable data. According to one aspect of the invention the items of data are medical data, e.g. images in acquired from various examinations such as CT or PET or in the form of written documents, e.g. laboratory reports, etc. However, the items of data should be interpreted to include any data to which the present invention can be usefully applied. Examples include any data that represent a snapshot of states of a system (such as machine). The state (open/closed) of a valve in a machine as recorded at discrete times separated by time units is one example for the items of data being represented as snapshots.

The term "data descriptor" as used in this disclosure should be interpreted as information describing one or more items of data. The data descriptors include, but are not limited to, metadata. Data descriptors can be obtained for example from the header of a DICOM file. A Header is a designated area within a file where such data descriptors are located. Examples for the data descriptors are patient identification, body part, type of examination, modality, and name of study. The "rank" of the medical data is another example of one of the data descriptors. The rank is being computed from a "time stamp", a feature explained below, of the medical data and a reference time, e.g. a user's local system time. The "rank" refers to either a "BASELINE" study, a "CURRENT" study or a "PRIOR" study. The BASELINE study refers to studies acquired before commencement of a treatment. The study is an item of medical data such as a CT or PET image created for the purpose of medical diagnosis of monitoring. The CURRENT study refers to the most recent study, whereas the "PRIOR" study refers to any study acquired prior to the current study. The data descriptor can be further qualified with numerals, such as PRIOR 1, PRIOR 2, in which the numbers indicate a sequence in which the study is carried out. For example, a PRIOR 2 study is older than a PRIOR 1 study, which is the most recent prior study.

The "Time stamp" is assigned to the items of data by an operating system and refers usually to a time at which the item of data has been last modified. In this disclosure, however, the term "time stamps" is given a slightly broader interpretation and is to be interpreted as the time assigned to the item of medical data which is indicative of when this item of medical data has been created.

"Graphics display" should be interpreted as a Graphical User Interface (GUI) allowing the user, such as the medical practitioner, to interface with a computer system.

"Interactive data elements" (IDE), "interactive timeline elements" (ITE) and "Timeline" refer to visual indicators which are known in the art as widgets. The widgets are basic components of the GUIs, which allow the user to execute a certain action in the computer system by using a navigation device, e.g. a computer mouse. A familiar example is retrieval of the item of data by clicking on a button using the computer mouse.

"Time points" are to be understood as the widgets indicating a time and arranged on the time line in a chronological order. The time indicated as time points may refer to the time stamps of the medical data. The time indicated on the time points may also refer to "representative time points", such as intervals, e.g. "week 1", "week 2", or to "medical time points". The "representative time points" are derived from the time stamps of the items of data. The medical time points are derived from time stamps in combination with other data descriptors, describing the medical information of the medical data such as the modality.

"Grouping" and "aggregating" refer to operations performed on the time stamps, the data descriptors or the other items of data by software modules according to the present invention. Resulting data structures are not necessarily stored permanently but are rather passed on by interfacing to other software modules. A familiar example is "piping" the UNIX commands "grep" and "sort" to produce an ordered list of files.

The operations of grouping and aggregating may also be performed on the time stamps in combination with other data descriptors, describing medical the medical information within the medical data such as the modality.

"Displaying" refers to interfacing with a GUI manager of the operating system of the computer system and other necessary steps for displaying the widgets, GUI etc. on the display device. In particular displaying is understood to comprise steps of ensuring that the widgets fit in designated areas (called "templates") within the graphics display. The steps include, but are not limited to, hiding the widgets or introducing scrolling elements for interactive rearrangement by the user of the widgets within the graphics display.

FIGS. 1-5 show various aspects and functionalities of a graphics display 100 according to one aspect of the present invention.

Figure 1:
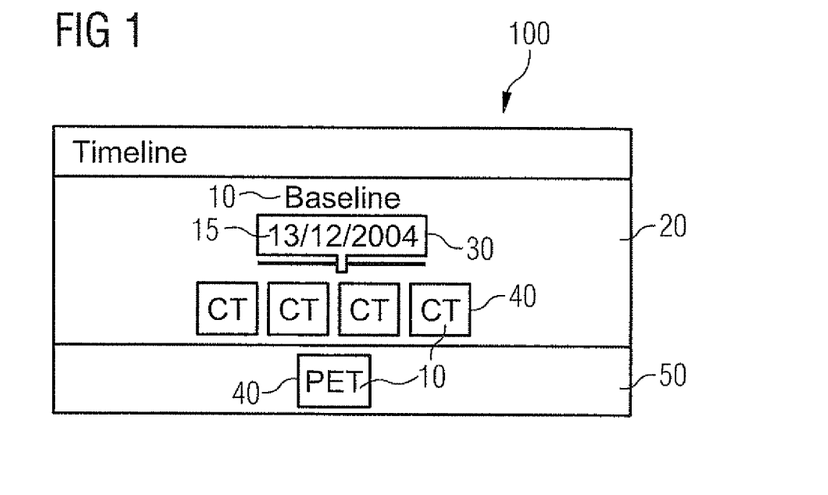
FIG. 1 is a schematic diagram illustrating the graphics display according to the present invention.

In FIG. 1 the graphics display 100 comprises an interactive time line (ITL) 20. On the ITL 20 there are arranged in a template 50 data descriptors 10 as interactive time line elements (ITE) 30 and interactive data elements (IDE) 40. The data descriptors 10 describe items of data 5. Some of the data descriptors 10 shown are the rank (in this example the BASELINE rank) and the data descriptors shown as IDEs 40 are modalities. In the example shown in FIG. 1, we have five items of data 5 of which four of the items of data have been acquired by a CT scan and one by PET means. One of the ITEs 30 is displayed as a time point 15. The time point 15 is representative of time stamps 6 of the items of data described by the data descriptors 10. In the example shown in FIG. 1, the ITE 30 is displayed as a time point 15, showing the token '13/12/2004', meaning that the five items of data 5 have been acquired on 13 Dec. 2004.

The items of data 5 are retrievable by navigating with a navigation device, for example a computer mouse. The items of data 5 are retrievable by selecting either the ITE 30 or the IDE 40. If a user, for example, double clicks on the ITE 30, a default item of data, described by one of the data descriptors, is retrieved. Upon retrieval, the item of data 5 is loaded into suitable post-processing software, for example, a viewer. In this way, the user can visually inspect the retrieved item of data. According to another aspect of the present invention, the user can "drag and drop" the IDE 40 into an already active instance of a viewer. According to another aspect of the present invention the ITE 30 or the IDE 40 show by means of a visual indication whether the item of data 5 has been retrieved.

Figure 2:
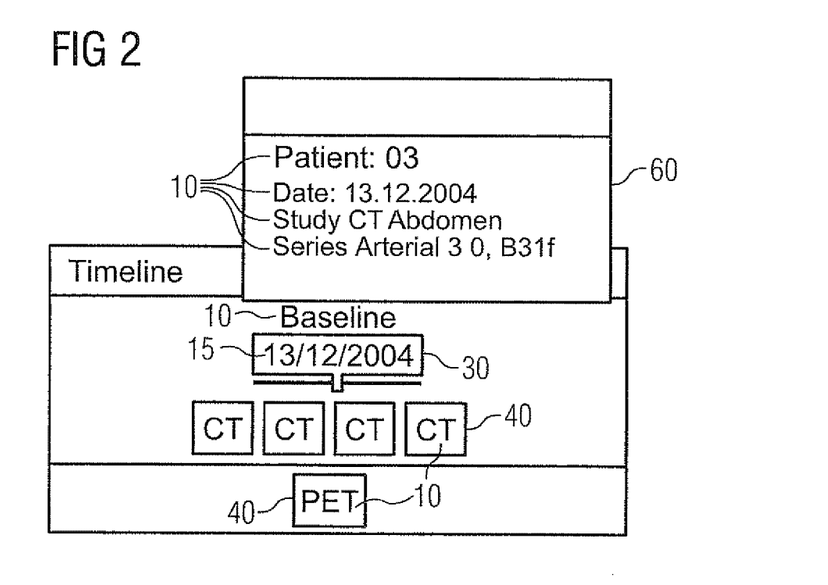
FIG. 2 is a schematic diagram illustrating a functionality provided by the graphics display of showing further details about the items of data.

FIG. 2 shows another aspect of the graphic display 100 according to the present invention. Further data descriptors 10 can be displayed in an overlay template by selecting the IDE 40 with a navigation device 120 in another mode. For example, the user can allow a pointer of a computer mouse to hover over the IDE 40 and the data descriptors 10 relating to the IDE 40 are displayed as a pop-up window in a tooltip fashion. In the example shown in FIG. 2, the overlay template 60 shows the further data descriptors 10 as a patient ID 705, a body part 710 and a study name 720.

Figure 7:
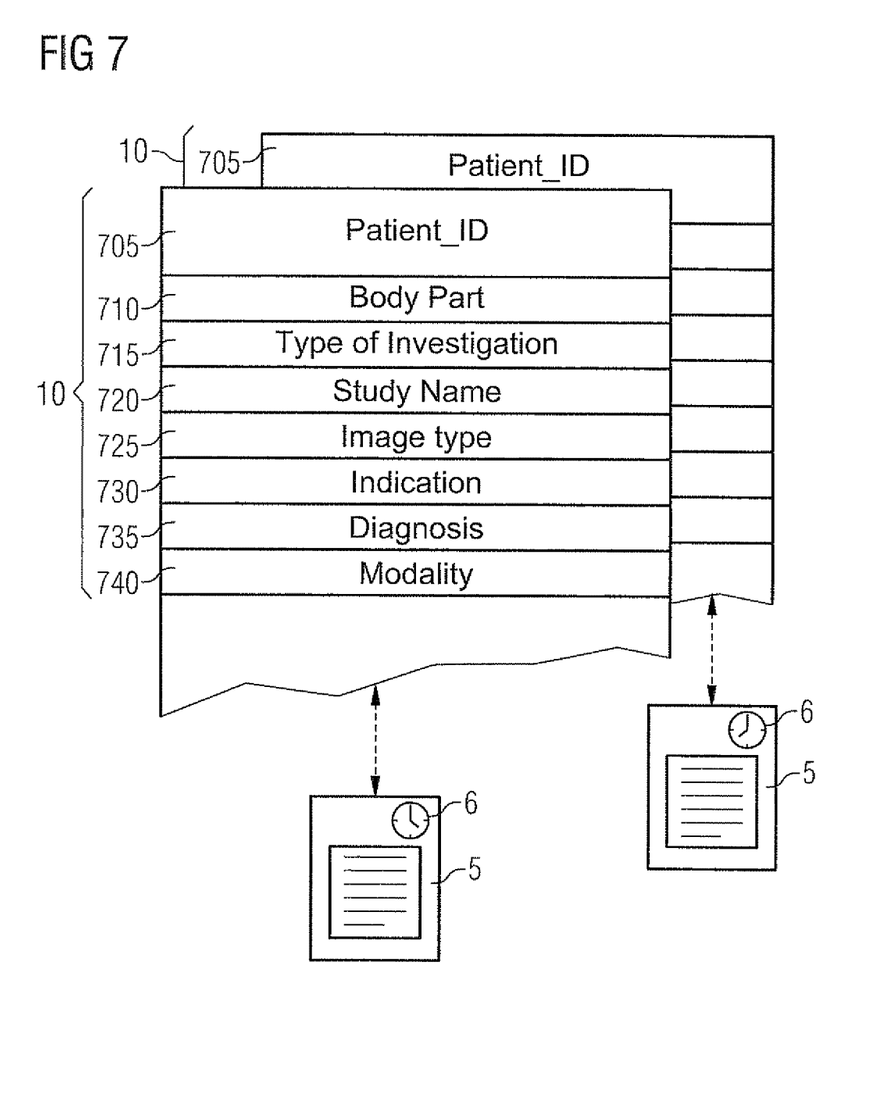
FIG. 7 is a schematic diagram illustrating the relationship of the items of data and the data descriptors

Further examples of the data descriptors 10 and the relation between data descriptors 10 and the items of data 5 are shown in FIG. 7: type of examination 715, Image ID 725, Diagnosis 735, 740 Modality.

Figure 3:
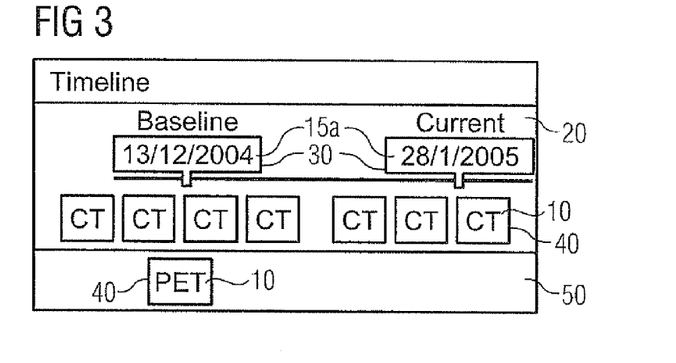
FIG. 3 is a schematic diagram illustrating a functionality provided by the graphics display of displaying multiple time points on the interactive timeline ITL within the graphics display.

Another aspect of the present invention is illustrated in FIG. 3. FIG. 3 shows a graphics display 100 with two time points 15. The data descriptors 10 are displayed in such a way that the data descriptors 10 can be visually associated with one of the two time points 15. The association of the data descriptors 10 is based on the time stamps 6 of the items of data 5 which are described by the data descriptors 10. In the example, illustrated in FIG. 3, there are three items of data 5 (which represent three CT images) that were acquired on 28 Jan. 2005 and five items of data 5 (which represent four CT images and one PET image) acquired on 13 Dec. 2004. According to one aspect of the present invention, the items of data 5 associated with different time points 15 can be retrieved by multi-selection. The user can compare easily the items of data 5 associated with different time points 15. For example, double clicking on the data descriptor 10, associated with the left one of the time points would load the CT image into the viewer. Double clicking on the data descriptor 10 associated with the right time point 15 would exchange the CT images shown in the viewer. In this way, the graphics display 100 supports toggling the viewer between the items of data 5 associated with different ones of the time points. According to another aspect of the invention the graphics display 100 can also interface with a double viewer. A double viewer is a viewer having two panes for comparing two of the items of data simultaneously. According to another aspect of the invention, the graphics display 100 allows to merge the data descriptors 10 describing the items 5 associated with different ones of the time points 15 into a single one of the time points 15. According to one aspect of the invention, this merging of ones of the time points 15 is done using the well-known technique of "drop-and-drag". One of the time points 15 the user wishes to merge is dragged and dropped on the other one of the time points 15 by means of the navigation device 120.

Figure 4:
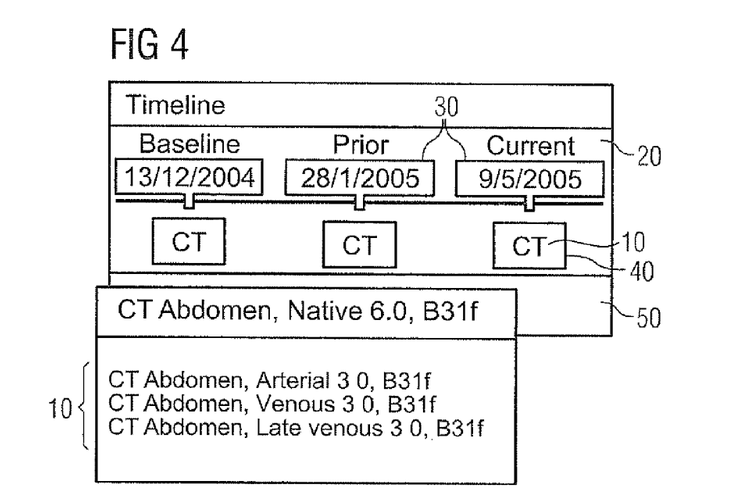
FIG. 4 is a schematic diagram illustrating a functionality provided by the graphics display of merging the overlay templates of various time points.

In FIG. 4 is shown another aspect of the present invention. It is shown a further functionality of merging the overlay template 60 from different ones of the time points 15 into a common overlay template. The totality of data descriptors 10 describing the items 5 of data associated with those different ones of the time points 15. Examination of the totality of data descriptors is made easier, the attention of the medical practitioner being directed to the common overlay display only.

Figure 5:
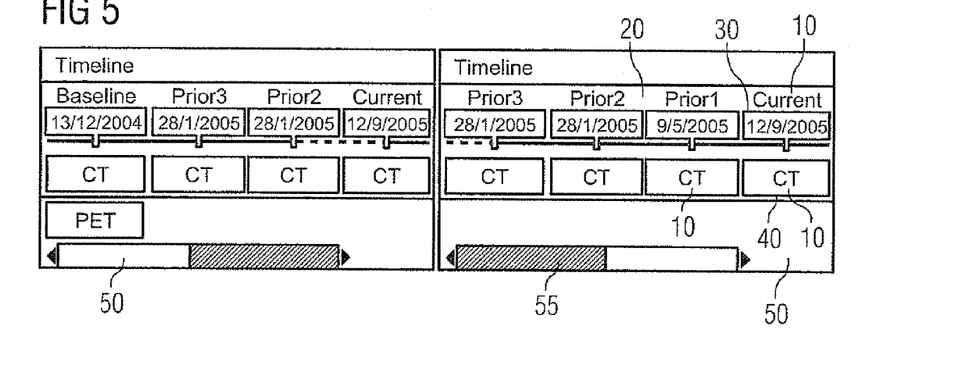
FIG. 5 is a schematic diagram illustrating a functionality provided by the graphics display of adjusting the template within the graphics display.

FIG. 5 shows another aspect of the present invention. The graphics display 100 offers a further feature of adjusting the template 50. If the user wishes to see additional ones of the time points 15 than can fit into the template 50, then either a scroll bar is added and/or some of the previously displayed time points 15 are hidden. The exact behaviour of the graphics display 100 is configurable by the user. In the example in FIG. 5 on the left hand side, the graphics display 100 is configured to permanently display certain designated ones of the time points 15. In this example the time points 15 associated with the items of data 5 ranked CURRENT and BASELINE are permanently displayed. Alternatively, on the right hand side of FIG. 5, the user configured the graphics display 100 such as to only show permanently the one of time point 15 associated with the items of data 5 ranked as CURRENT. Therefore, the time point 15, associated with the items of data 5 ranked BASELINE, is not shown, but rather a further one of the time points 15, associated with the items of data 5 ranked PRIOR, in this case PRIOR 3, is shown instead.

As explained above, the rank of data item 5 (BASELINE, CURRENT, PRIOR) is a data descriptor 10 being derived from the time stamp 6 and the user's local system time.

Figure 6:
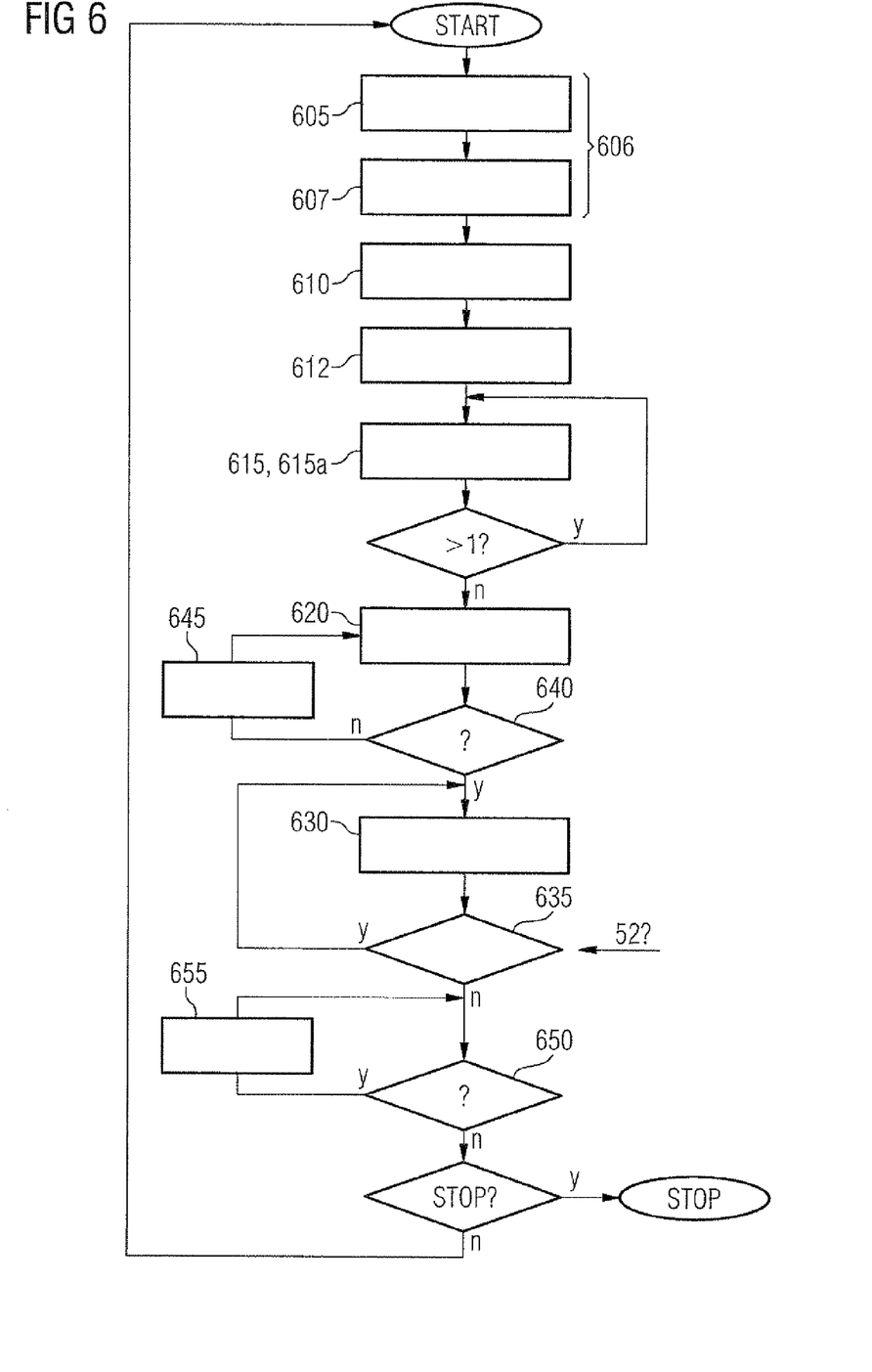
FIG. 6 is a high-level flow chart of the functionalities of the graphics display.

FIG. 6 shows a high level flow chart of the functions of the software modules implementing the graphics display 100 according to the present invention. The graphics display 100 receives in step 605 from the user an adjustable time unit 25. The adjustable time unit 25 allows the adjusting of a time resolution on the ITL 20 of the graphics display 100. The user further provides some of the data descriptors 10, which describe the items of data 5 s/he wishes to examine. For example, the user might query a data store for a patient identify cation 705 and for a modality 740. The items of data 5 matching the query are either retrieved locally or references to the items of data 5 are returned. The items of data 5 are selected in step 606. The selection is done by performing to steps. In step 607 the items of data are grouped according to their time stamps 6. Any two items of data 5 are grouped together if the time stamps 6 of each of the two items of data are indicative to a time within a multiple of the time unit 25, the time unit 25 being reckoned from a user's local system time. In this way, the items of data 5 can be four example grouped into weekly intervals. if the time unit 25 equals a week.

The data descriptors 10 describing the grouped items of data 5 are then aggregated in step 610. The operations of grouping and aggregating are logical operations for building references to the corresponding items of data 5 rather than forming permanently stored groups and aggregates of the items of data 5. The graphics display 100 displays in step 615 the time point 15 on the ITL 20 as the ITE 30. The time point 15 is chosen to be representative of the time stamps 6 of the grouped items of data 5 described by the aggregated data descriptors 10. By means of the grouped time stamps 6, a relation is established between the representative time point 15 and the aggregated data descriptors 10. The representative time point 15 is either taken as any one of the time stamps 6 of the grouped items of data 5 or as a multiple of the received time unit 25. In this way, the user can decide to choose daily, weekly, monthly, etc. time resolution on the ITL 20. The time intervals determined by the received time unit are reckoned with reference to the user's local system time. According to another aspect of the invention, the representative time point 15 is taken to be a medical time point. According to this aspect of the invention, the step 607, groups the items 5 of data not only on the basis of the time stamps 6 but in combination with pre-definable rules and those data descriptors 10 describing medical information within the grouped items 5 of data. The pre-definable rules are fetched, in an intermediary step (not shown), e.g. from a medical database (not shown). The pre-defined rules prescribe, based on the data descriptors 10, which items of data 5 are to be examined in conjunction and prescribe time margins, which are to be observed in combination with the time stamps 6 in step 607 when the items of data 5 are grouped. If the time stamps 6 of ones of the items of data 5 described by certain ones of the data descriptors 10 differ by less than the time margin, then the those ones of the items of data 5 have to be grouped together. For example, it may be necessary for medical reasons to examine CT and PET images in conjunction and hence to have graphics display 100 group in step 607 the CT and PET images together so that they get associated with the same time point 15. Had step 607 grouped the CT and PET images solely on the basis of their respective time stamps 6, the CT and PET images would have been associated with different ones of the time points 15. In this case, the time point 15 is referred to as a medical time point 15.

The graphics display 100 then displays in step 620 the aggregated data descriptors as the IDEs 40 within the template 50. According to one aspect of the invention, the time point 15 is visually associated with the aggregated data descriptors 10 displayed as the IDEs 40. For example, on FIG. 1 the IDEs 40 are displayed underneath the time point 15. However, other arrangements that allow the user to easily understand the association between the time points 15 and the IDEs 40 are also within the scope of the invention. In order to assist the user in examining the items of data 5 the invention automatically suppresses display in step 615 of the time points 15 if there are no items of data 5 associated with the time points 15. The graphics display 100 displays in step 630 a further template 60 displaying further ones of the data descriptors 10 if an event 52 is detected in step 635. Such an event can be triggered, for example, by selecting the IDE 40 with the navigation device 120. Additional ones of the time points 15 are displayed in step 640 on the ITL 20 if the additional ones of the time points fit into the template 50. Otherwise, a format of the template 50 is adjusted in step 645 by, for example, hiding some of the IDEs 40 or by providing a scrolling element 55. Upon receiving in step 650 an ITE event 30a the item of data 5 is being retrieved. The ITE event 30a is indicative to the navigation device 120 interacting with an ITE 30. The ITE event 30a triggers retrieving in step 655 of an item of data 5 associated with the time point 15 displayed as the ITE 30. The invention therefore provides an alternative way to retrieve the items of data 5 other than using the IDEs 40 described above.

According to one aspect of the invention a visual indication on the one of the ITEs 30 is provided if the item of data 5 was retrieved in step 655 using the ITE 30. Retrieving in step 655 multiple ones of the items of data 5 using different ones of the ITEs 30 is also supported by another aspect of the invention. Another aspect of the invention allows the user to interact with the ITL 20 itself via the navigation device 120. For example double-clicking the ITL 20 using the computer mouse allows the user to toggle between a "basic" view and an "extended" view on the ITL 20. The extended view displays more or all of the data descriptors 10 as the IDEs 40 associated with the time points 15. In the "basic" view, on the other hand, the ITL 20 is collapsed to merely show a few exemplary IDEs 40 for ease of navigation for the user.

Figure 8:
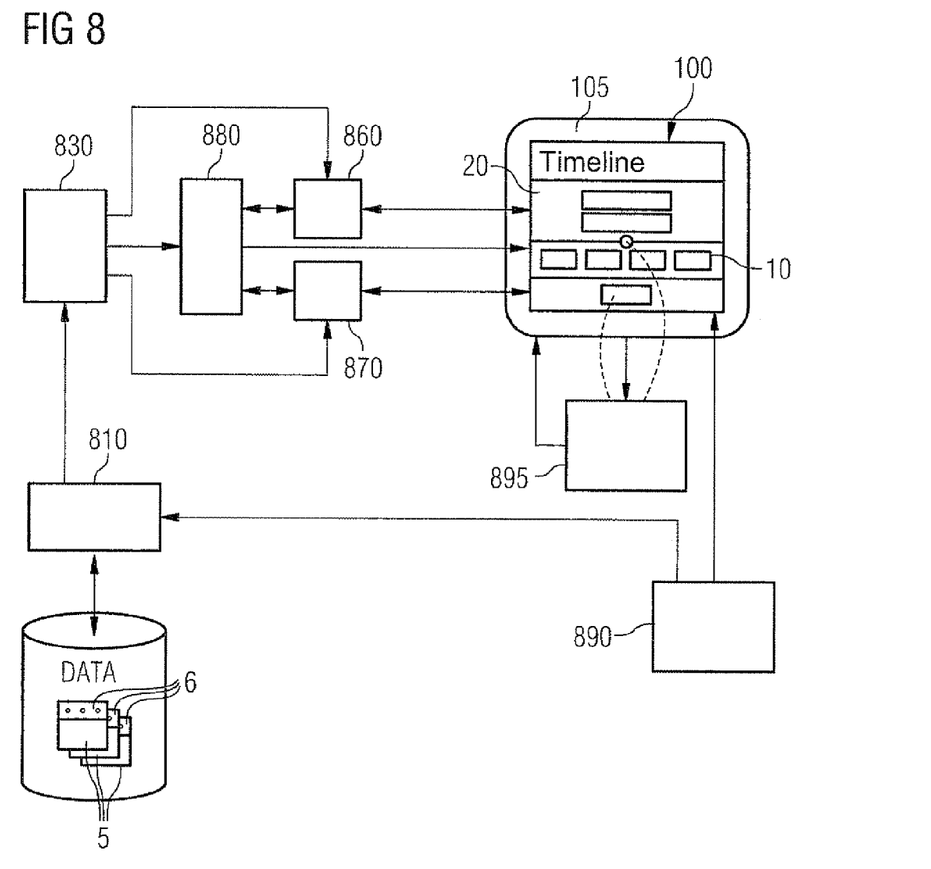
FIG. 8 is a functional block diagram showing the interactions between the software modules implementing the graphics display according to one aspect of the present invention.

FIG. 8 shows the interfacing of the software modules implementing the functions of the graphics display 100 as explained above.

Initial input from the user is received via the user data interface 890. This could include, for example the time unit 25 and, optionally, a set of set-up parameters to configure the behaviour of the graphics display 100 such as default values etc. A user data interface 980 interfaces also with the data interface module 810 and passes on a set of the data descriptors 10 so that a data interface module 810 can search and retrieve the items of data 5. Once the items of data 5 or references to the items of data 5 are retrieved the data interface module 810 performs the grouping of step 607 of the items of data 5. Upon interfacing with the data aggregator module 830 the data descriptors 10 are aggregated in step 610. Information about the aggregated descriptors are piped into a time graphics display manager 860 and a data graphics display manager 870 to produce respectively the displaying of step 615 and the displaying of step 620 on the ITL 20 of the time points 15 as ITEs 30 and the data descriptors 10 as IDEs 40. A master graphics display manager 880 provides for visual association on the ITL 20 of time points 15 to related ones of the data descriptors 10 in the manner explained above. The application manager 895 intercepts events 52 and 30a from the ITEs 30 or the IDEs 40 (or the ITL 20 according to one aspect of the invention) and is responsible for loading, upon retrieval of a particular item of data 5, an appropriate viewer. The appropriateness of the viewer is established by attaching messages to the events 52 and 30a in which the messages comprising the data descriptors 10 describing, for example, the data type of the item of data 5.

According to one aspect of the invention, the application manager 895 interfaces with the viewer to learn about the viewer's functionalities. For example, having learned that the viewer is the double viewer, the application manager 895 will load two of the items of data retrieved by multi selection of two of the ITEs 30 into one instance of the double viewer. This functionality facilitates comparison between items of data 5 having been retrieved 655 using different ones of the ITEs 30 or IDEs 40.

Other aspects of the invention, which implement the system in hardware, firmware, or a combination of both, hardware and software, as well as distributing the modules and/or the data in a different fashion will be apparent to those skilled in the art and are also within the scope of the invention.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for displaying a plurality of data descriptors arranged on an interactive timeline comprising a plurality of interactive timeline elements associated with time points, comprising:
    displaying one of the time points as one of the interactive timeline elements;
    selecting one of the data descriptors associated with the displayed time point;
    displaying the selected data descriptor in a template as one of interactive data elements;
    selecting a further one of the data descriptors associated with the displayed time point;
    displaying the further selected data descriptor,
    wherein the data descriptors describe items of data having time stamps and the items of data is retrieved based on the interactive data elements,
    wherein the steps of selecting comprises:
        grouping the items of data based on the time stamps and a pre-defined rule prescribing a grouping relation between the data descriptors, and
        aggregating the data descriptors describing same items of the grouped items of data as the further selected data descriptor,
    wherein one of the same items of the grouped items of data is retrieved based on a further one of the interactive timeline elements and displayed as a further time point,
    wherein the further displayed time point is suppressed if there are no same items of the grouped items of data,
    wherein the same items of the grouped items of data are compared by a double viewer having two panes for showing the same items of the grouped items of data simultaneously,
    wherein the further selected data descriptor is displayed in a further template, and
    wherein the template and the further template are merged into a common display template for directing a medical practitioner to the common display template only.

2. The method as claimed in claim 1, wherein the displayed time point represents the time stamps of the same items of the grouped items of data.

3. The method as claimed in claim 1,
    wherein one of the same items of the grouped items of data is retrieved based on a further one of the interactive timeline elements and displayed as a further time point, and
    wherein the further displayed time point is:
        arranged on the interactive timeline chronologically, and
        visually associated with the further selected data descriptor.

4. The method as claimed in claim 3, wherein the displayed time point is displayed visually separately from the interactive timeline in the template after retrieval.

5. The method as claimed in claim 3,
    wherein the further displayed time point is displayed in the template if the further one of the interactive timeline elements is displayable in the template,
    wherein a format of the template is adjusted if the further one of the interactive timeline elements is not displayable in the template, and
    wherein the adjustment of the format comprises hiding one of the interactive time line elements or adding a scrolling element to the template.

6. The method as claimed in claim 1, wherein an interactive time line event is received by interacting with one of the interactive timeline elements and one of the items of data associated with one of the time points is retrieved based on the interactive timeline event.

7. The method as claimed in claim 1, wherein a time unit is received by adjusting a time resolution on the interactive timeline.

8. The method as claimed in claim 1, wherein the items of data are items of medical data.

9. The method as claimed in claim 1, wherein the data descriptors comprise metadata.

10. The method as claimed in claim 1, wherein the selected data descriptor is merged with the further selected data descriptor.

11. The method as claimed in claim 1,
    wherein the data descriptors comprises a rank computed from the time stamp referring to a baseline study, a current study, or a prior study,
    wherein the baseline study refers to a study acquired before a treatment, wherein the current study refers to a study acquired most recently, and wherein the prior study refers to a study acquired prior to the current study.

12. A computer readable medium executed in a computer for displaying a plurality of data descriptors arranged on an interactive timeline comprising a plurality of interactive timeline elements associated with time points, comprising:
   a computer program that:
      instructs a display of one of the time points as one of the interactive timeline elements;
      selects one of the data descriptors associated with the displayed time point;
      instructs a display of the selected data descriptor in a template as one of interactive data elements;
      selects a further one of the data descriptors associated with the displayed time point; and
      instructs a display of the further selected data descriptor,
   wherein the data descriptors describe items of data having time stamps and the items of data is retrieved based on the interactive data elements,
   wherein computer program further:
      groups the items of data based on the time stamps and a pre-defined rule prescribing a grouping relation between the data descriptors, and
      aggregates the data descriptors describing same items of the grouped items of data as the further selected data descriptor,
   wherein one of the same items of the grouped items of data is retrieved based on a further one of the interactive timeline elements and displayed as a further time point, and
   wherein the further displayed time point is suppressed if there are no same items of the grouped items of data,
   wherein the same items of the grouped items of data are compared by a double viewer having two panes for showing the same items of the grouped items of data simultaneously,
   wherein the further selected data descriptor is displayed in a further template, and
   wherein the template and the further template are merged into a common display template for directing a medical practitioner to the common display template only.

13. A system for displaying a graphics display of a plurality of data descriptors, wherein the data descriptors describes items of data having time stamps and is arranged on an interactive timeline comprising a plurality of interactive timeline elements associated with time points, the system comprising:
   a data interface module that groups the items of data based on the time stamps;
   a data aggregator module that aggregates ones of the data descriptors describing same items of the grouped items of data;
   a time graphics display device that displays one of the time points as one of the interactive timeline elements on the interactive timeline, the time point representing the time stamps of the same items of the grouped items of data; and
   a data graphics display device that displays the aggregated data descriptors in a template as one of interactive data elements,
   wherein one of the same items of the grouped items of data is retrieved based on a further one of the interactive timeline elements and displayed as a further time point, and
   wherein the further displayed time point is suppressed if there are no same items of the grouped items of data,
   wherein the same items of the grouped items of data are compared by a double viewer having two panes for showing the same items of the grouped items of data simultaneously,
   wherein the further selected data descriptor is displayed in a further template, and
   wherein the template and the further template are merged into a common display template for directing a medical practitioner to the common display template only.

14. The system as claimed in claim 13, further comprising a master graphics display device that associates the displayed time point with the displayed aggregated data descriptors.

15. The system as claimed in claim 13, further comprising:
   a user data interface that receives an adjustable time unit for adjusting a time resolution on the interactive timeline,
   a navigation device that indicates an interactive time line event interacting with one of the interactive timeline elements, and
   an application device that receives the interactive time line event for retrieving one of the items of data.

16. The system as claimed in claim 15, wherein the navigation device is selected from the group consisting of: a cursor, a pointer, and a touch screen.

17. The system as claimed in claim 13, wherein the items of data are selected from the group consisting of: a patient identification, a patient's body part, a type of examination, a name of study, a medical image, an indication, and a diagnosis.

* * * * *